United States Patent [19]

Hammell

[11] 4,298,604
[45] Nov. 3, 1981

[54] CLOTRIMAZOLE-BETAMETHASONE DIPROPIONATE COMBINATION

[75] Inventor: Susan B. Hammell, Berkeley Heights, N.J.

[73] Assignee: Schering Corporation, Kenilworth, N.J.

[21] Appl. No.: 194,524

[22] Filed: Oct. 6, 1980

[51] Int. Cl.³ .................... A61K 31/56; A61K 31/58
[52] U.S. Cl. ................................................ 424/240
[58] Field of Search .................. 424/240; 260/397.45

[56] References Cited

U.S. PATENT DOCUMENTS 3,784,692 1/1974 Ercoli et al. .................. 424/243
4,018,918 4/1977 Ayer et al. .................... 424/240

*Primary Examiner*—Elbert L. Roberts
*Attorney, Agent, or Firm*—Paul H. Ginsburg

[57] ABSTRACT

Antifungal compositions comprising clotrimazole and betamethasone dipropionate are disclosed.

6 Claims, No Drawings

CLOTRIMAZOLE-BETAMETHASONE DIPROPIONATE COMBINATION

The present invention relates to antifungal compositions comprising clotrimazole, a synthetic antifungal agent, and betamethasone dipropionate, a corticosteroid. Such compositions are surprisingly more effective against fungi than compositions comprising only clotrimazole.

The compositions of the present invention comprise about 0.001 to about 0.33 percent by weight betamethasone dipropionate and about 0.01 to about 10 percent by weight clotrimazole in a pharmaceutically acceptable carrier. Preferably, the compositions of the present invention comprise about 0.01 to about 0.1 percent by weight betamethasone diproprionate and about 0.1 to about 2 percent by weight clotrimazole. In the compositions of the present invention, the ratio of clotrimazole to betamethasone dipropionate ranges from about 10 to 1 to about 30 to 1. A particularly preferred composition comprises about 0.06 percent by weight betamethasone dipropionate and about 1 percent by weight clotrimazole.

The compositions of the present invention may be used in the topical treatment of the following derma and/or vaginal infections: tinea pedis, tinea cruris, and tinea corporis due to, for example, *Trichophyton rubrum, Trichophyton mentagrophytes, Epidermophyton floccosum,* and *Microsporum canis;* candidiasis due to *Candida albicans;* and tinea versicolor due to Malassezia furfur. The compositions of the present invention are particularly useful when these infections are accompanied by moderate to severe inflammation.

Depending on the severity of the infection, the present compositions may be administered one or more times per day for a period ranging from a few days to several weeks until sufficient improvement is obtained, depending upon the judgment of the attending clinician. The compositions may be administered topicaly in the form of creams, ointments, lotions, solutions, aerosol sprays, and the like. Although an ointment is likely to be the most effective vehicle, because of the occlusive effect of the anhydrous petrolatum vehicle, a cream or lotion is likely to be more esthetically acceptable to the patient. For vaginal administration, the use of tablets, suppositories or coated condoms may also be advantageous.

The following Example gives illustrative formulations, at five concentrations, of the compositions of the present invention. All weights are given in miligrams. Cream, ointment and lotion formulations having the same identifying letter have the same concentration of active ingredients. The following ingredients are combined and packaged by standard techniques, well-known to those skilled in the art, to give the cream, ointment or lotion, as requird. The dashes in columns B, C, D and E indicate that the weight of a particular ingredient is the same as that in column A.

EXAMPLE

| | A | B | C | D | E |
|---|---|---|---|---|---|
| Cream | | | | | |
| Betamethasone Dipropionate | 0.0100 | 10.0 | 0.100 | 1.00 | 0.643 |
| Clotrimazole | 0.100 | 100 | 1.00 | 20.0 | 10.0 |
| Mineral Oil | 60.0 | — | — | — | — |
| Petrolatum | 150 | — | — | — | — |
| Cetostearyl Alcohol | 72.0 | — | — | — | — |
| Polyethylene Glycol 1000 Monocetyl Ether | 22.5 | — | — | — | — |
| Benzyl Alcohol | 10.0 | — | — | — | — |
| Sodium Phosphate Monobasic Monahydrate | 2.65 | — | — | — | — |
| Phosphoric Acid | 0.0200 | — | — | — | — |
| Propylene Glycol | 100 | — | — | — | — |
| Purified Water | to make 1 gram | — | — | — | — |
| Ointment | | | | | |
| Betamethasone Dipropionate | 0.0100 | 10.0 | 0.100 | 1.00 | 0.643 |
| Clotrimazole | 0.100 | 100 | 1.00 | 20.0 | 10.0 |
| Mineral Oil | 50.0 | — | — | — | — |
| Petrolatum | to make 1 gram | — | — | — | — |
| Lotion | | | | | |
| Betamethasone Dipropionate | 0.0100 | 10.0 | 0.100 | 1.00 | 0.643 |
| Clotrimazole | 0.100 | 100 | 1.00 | 20.0 | 10.0 |
| Mineral Oil | 10.0 | — | — | — | — |
| Cetostearyl Alcohol | 3.00 | — | — | — | — |
| Polyethylene Glycol 1000 Monocetyl Ether | 10.0 | — | — | — | — |
| Benzyl Alcohol | 10.0 | — | — | — | — |
| Sodium Phosphate Monobasic Monohydrate | 2.65 | — | — | — | — |
| Phosphoric Acid | 0.0200 | — | — | — | — |
| Propylene Glycol | 100 | — | — | — | — |
| Purified Water | to make 1 gram | — | — | — | — |

I claim:

1. A pharmaceutical composition comprising about 0.001 to about 0.33 percent by weight betamethasone dipropionate and about 0.01 to about 10 percent by weight clotrimazole, wherein the ratio of clotrimazole to betamethasone dipropionate ranges from about 10 to about 30 to 1, in a pharmaceutically acceptable carrier.

2. A composition according to claim 1, wherein the concentration of betamethasone dipropionate is about 0.01 to about 0.1 percent by weight and the concentraton of clotrimazole is about 0.1 to about 2 percent by weight.

3. A composition according to claim 1, wherein the concentration of betamethasone is about 0.06 percent by weight and the concentration of clotrimazole is about 1 percent by weight.

4. A composition according to claim 1 in the form of a cream.

5. A composition according to claim 1 in the form of an ointment.

6. A composition according to claim 1 in the form of a lotion.

* * * * *

REEXAMINATION CERTIFICATE (3690th)
United States Patent [19]

Hammell

[11] B1 4,298,604

[45] Certificate Issued  Dec. 22, 1998

[54] CLOTRIMAZOLE-BETAMETHASONE DIPROPIONATE COMBINATION

[75] Inventor: Susan B. Hammell, Berkeley Heights, N.J.

[73] Assignee: Schering Corporation, Kenilworth, N.J.

Reexamination Request:
No. 90/004,624, May 8, 1997

Reexamination Certificate for:
Patent No.: 4,298,604
Issued: Nov. 3, 1981
Appl. No.: 194,524
Filed: Oct. 6, 1980

[51] Int. Cl.$^6$ .................. A61K 31/56; A61K 31/415; A61K 31/58
[52] U.S. Cl. ................................. 514/180; 514/396
[58] Field of Search ............................. 514/180, 396

[56] References Cited

FOREIGN PATENT DOCUMENTS

A-1 767 326  9/1971  Germany.
A-2 615 140  10/1976  Germany.

OTHER PUBLICATIONS

H. Weuta, et al., "Baycuten–Klinische Wirkung Und Verträglichkeit," Med. Welt, vol. 29, pp. 1013–1015 (1978).

V. de Arruda Zamith "Ensaio Clinico Sobre a Eficacia e Tolerancia do Baycuten", Revista Brasileira de Medicina, vol. 35, No. 10, pp. 625–626 (1978).

A. Parreira, "Estudo Clinico Sobre a Eficacia e Tolerancia do Baycuten", Revista Braseleira de Medicina, vol. 35, No. 10, pp. 614–615 (1978).

H. Szarmach, et al., "Klinische, Bakteriologische Und Histologische Untersuchungen Bei Der Anwendug Von Baycuten–Creme," Med. Welt, vol. 31, No. 48, pp. 1763–1766 (Nov. 1980).

M. Polkowska, et al. "Baycuten Und Baycuten SD Wirkung Und Veträglichkeit," Med. Welt, vol. 33, No. 14, pp. 525–529 (1982).

M. Polkowska, "Kliniczna Ocena Preparatow Baycute I Baycuten SD", Przegl Dermatol., vol. 71, pp. 483–486 (1984).

N. Balato, et al., "Valutazione Dell'associazione Desametasone Acetato, Clotrimazolo, Azidamfenicolo Per Uso Topico", Derm. Clin. No. 3, pp. 267–272 (1984).

M. Polkowska, et al., "Behadlung Von Lichen Sclerosus et Atrophicus Und Pruritius Der Genitalgegend Mit Baycuten" Med. Welt, vol. 37, pp. 812–814 (1986).

C. Raulin, et al. "Kontaktallergie Auf Clotrimazole Und Azidamfenicol" Dermatosen, vol. 35, No. 2 (1987).

F. Bahmer, "Vergleichende Studie Zur Wirksamkeit Von Lotricomb Und Baycuten Für Die Behandlung Superinfizierter Ekzeme," Akt. Dermatol. vol. 15, pp. 294–296 (1989).

"Therapieverkürzung Der Dermatomykose Durch Zweerkombination", Therapiewoche, vol. 40, No. 8, p. 494 (1990).

G. Wozel, "Topische Kombinationspräparate Bei Dermatomykosen: Antimykotica Und Glukokortikosteroide", Sozialpädiatrie, vol. 16, No. 10, pp. 610–613 (1994).

W. Hesseling, et al., "Ekzetherapie Mit Baycuten Und Baycuten SD", Med. Welt vol. 30, pp. 581–586 (Apr. 1979).

H. Sauer, "Kombinationsbehandlung Genitoanaler Ekzeme Mit Baycuten Und Baycuten SD," Therapiewoche, vol. 29, pp. 4550–4554 (Sep. 1979).

A Bjornberg et al., "Diproderm With Gentamicin—A New Very Potent Steroid Ointment in Infected Eczema," Current Therapeutic Research, vol. 18, No. 4 (1975).

Unlisted Drugs, vol. 27, No. 1 p. 5 (Jan. 1975).

Dictionnaire Vidal, 1975, p. 536.

"Internordiskt Dermatologiskt 'Round Table' Betraffande Kombinationsterapi Mellan Kortikoider Och Antimikrobiella Medel Med Särskild Hansyn Till Indikationen 'Inflammerade Mykoser'" Kopenhagen (Feb. 11, 1980).

W. Raab, "Clinical Pharmacology of Modern Topical Broad–Spectrum Antimicrobials," Current Therapeutic Research, vol. 22, N. 1, pp. 65–82 (1977).

W. Rabb, "Breitspektrumantimyzetika Und Glukokortikoide," Zentralblatt Haut Und Geschlechtskrankheiten vol. 144, pp. 87–96 (Oct. 1980).

"Mykosebahandlung Mit Imidazolderivaten", W. Rapp, pp. 162–164 (1978).

H. Weitgasser, et al., "Vergleichende Klinische Untersuchungen Mit Dem Neuen Antimykotikum Isoconazolnitrat Und Seiner Kombination Mit Difluocortolon–21–Valerat Bei Entzündlichen Und Ekzematisierten Dermatoykosen", Mykosen, vol. 22, No. 6, pp. 177–183 (1979).

L. Gip, et al., "Ergebnisse Eines Halbeitenvergleichs Zwischen Travocort® Creme Und Travogen® Creme Bei Entzündlichen Und Ekzematisierten Dermatmykosen," Mykosen, vol. 23, No. 2, pp. 79–84 (1980).

W. Rabb, "Glucocorticoids and Antimicrobials", Mykosen, Suppl. 1, pp. 304–310 (1978).

Raab, W. et al. "Intractions between Econazole and Topically Active Glucocorticoids", Dermatologica 153:14–22 (1976).

Martin du Pan, R., et al. "Diaper Dermatitis and its Treatment with an Anti–Infective/corticosteroid Combination Cream", Pharmacotherapeutica 2:247–252 (1979).

Fredriksson, T. "Treatment of Dermatmycoses with Topical Econazole Combined wita Steroid as compared with a Conventional Oxichinoline–steroid Combination", Current Therapeutic Research 26:958–961 (1979).

Grigoriu, D. et al., "Follow–up Study of 100 Patients Treated for Superficial Mycoses" Dermatologica 160:62–68 (1980).

Mertens, R.L., et al. "A Double Blind Study Comparing Daktacort, Miconazole, and Hydrocortisone in Inflammatory Skin Infections" Dermatologica 153:228–235 (1976).

Fishman, Olga, et al., "Daktaort in Skin Lesions", Mykosen 20:471–475 (1977).

(List continued on next page.)

*Primary Examiner*—William R. A. Jarvis

[57]  ABSTRACT

Antifungal compositions comprising clotrimazole and betamethasone dipropionate are disclosed.

OTHER PUBLICATIONS

McVie, D. et al., "Daktacort in Inflammatory Skin Disease," Britsh J of Clinical Practice, 353–357 (1979).

Pastinszky, I. et al. "Therapeutic Value of Mycosolon Ointment in the Treatment of Dermatomycoses" Ther. Hung. 25:51–54 (1977).

Vankos, J., et al. "Experimental and Clinical Data on Mycosolon Ointment" Ther. Hung. 23:71–76 (1975).

Maibach, H. "Iodochlorhydroxyquin–Hydrocortisone Treatment of Fungal Infections", Arch. Dermatol. 114:1773–1775 (1978).

Pettit, J.H.S. "Treatment of Superficial Fungal Infections of the Skin" Drugs 10:130–142 (1975).

Young, M., et al. "Misdiagnosed Dermatophytosis" Journal of Infection 4:127–129 (1982).

Guette, D. et al., "Adverse Effects of Corticosteroids" Cutis 23:477–487 (1979).

Carpenter, C.L. et al., "A Double Blind Multicenter Study of Iodochlorhydroxyquin–Hydrocortisone in 277 Patients", Current Therapeutic Research 15:650–659 (1973).

Miller, R.C. "Flumethasone pivalate–Iodochlorhydroxyquin Cream. A New Corticosteroid Anti–Infective Combination" Cutis 14:605–609 (1974).

Knopka et al "Antimicrobial Effectiveness of Locacorten–Vioform Cream in Secondary Infections of Common Dermatoses" Dermatologica 151:1–8 (1975).

Wortzel, M.H. "A Double Blind Study Comparing the Combination Antifungal (Clotrimazole)/Steroid (Betamethasone dipropionate) to its Components" Cutis 30:258–261 (1982).

Physicians' Desk Reference, 31st Edition, 1977, pp. 750, 1393–1394.

Compendium of Pharmaceuticals and Specialties, Canada, 13th Ed., 1978, pp. v, vi, xi, 102–103 and 201.

Drug Index for Malaysia and Singapore, vol. 70, No. 3, Sep. 1978, p. 246.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–6 is confirmed.

* * * * *